(12) United States Patent
Pascale

(10) Patent No.: US 10,470,919 B2
(45) Date of Patent: Nov. 12, 2019

(54) PORTABLE MALE URINATION APPARATUS

(71) Applicant: Steven Patrick Pascale, San Clemente, CA (US)

(72) Inventor: Steven Patrick Pascale, San Clemente, CA (US)

(73) Assignee: Steven P. Pascale, San Clemente, CA (US)

( * ) Notice: Subject to any disclaimer, the term of this patent is extended or adjusted under 35 U.S.C. 154(b) by 646 days.

(21) Appl. No.: 14/545,902

(22) Filed: Jul. 6, 2015

(65) Prior Publication Data

US 2017/0007441 A1    Jan. 12, 2017

(51) Int. Cl.
*A61F 5/453* (2006.01)
*A61F 5/44* (2006.01)
*A61G 9/00* (2006.01)
*A61B 5/107* (2006.01)
*A61B 5/00* (2006.01)

(52) U.S. Cl.
CPC ............ *A61F 5/453* (2013.01); *A61F 5/4405* (2013.01); *A61G 9/006* (2013.01); *A61B 5/1072* (2013.01); *A61B 5/4375* (2013.01)

(58) Field of Classification Search
CPC ...... A61F 5/453; A61F 5/4405; A61F 5/4556; A61G 9/006
USPC .................................. 4/144.1, 144.3, 144.4
See application file for complete search history.

(56) References Cited

U.S. PATENT DOCUMENTS

| | | | | |
|---|---|---|---|---|
| 2,358,850 A * | 9/1944 | Chenault | ................ | A61G 9/006 222/638 |
| 4,091,476 A * | 5/1978 | DeBurgh | ............... | A61G 9/006 4/144.3 |
| 6,026,519 A * | 2/2000 | Kaluza | ................... | A61G 9/006 4/144.1 |
| 2011/0060297 A1* | 3/2011 | Glenn | .................... | A61G 9/006 604/317 |
| 2011/0137272 A1* | 6/2011 | Adams | .................. | A61G 9/006 604/349 |
| 2012/0165768 A1* | 6/2012 | Sekiyama | ............... | A61F 5/453 604/353 |

\* cited by examiner

*Primary Examiner* — Matthew F Desanto

(57) ABSTRACT

A portable male urination container. Having a top funnel opening with accompanied lid enclosure. Liquid is contained within a collection chamber. The container includes two handles which provide a means for stable operations as well as preventing any spillage. The urinal is ideal for potty-training when bathroom facilities are impracticable for teaching purposes.

4 Claims, 7 Drawing Sheets

PORTABLE MALE URINATION APPARATUS

BACKGROUND OF THE INVENTION

1. Field of Invention

The present disclosure relates generally to an apparatus associated with portable urinal devices and medical disposal containers as well as method for measuring a given penis for condom and catheter purposes.

2. Description of Related Art

Assorted portable urinal apparatus have been developed for use in the absence of an ergonomic device. Usage includes cars, trucks, boats, golfing carts as well as "other" outdoor activities like camping. Adequate toilet facilities therein oftentimes can present issues. In a somewhat different setting, bedridden hospital patients utilize a pan receptacle. Such urinals designs have been used for a significant amount of time (years) with no modifications. Another example is the "cup" used in doctor offices. Perplexing in size, these container(s) often are used to catch mid-stream urine and presents a challenge in repositioning a given cup once it has been filled.

Similarly, pilots flying many type of small aircraft are without bathroom facilities. During long flights or military missions, the problem can be particularly acute. Currently, some Navy and Air Force fliers are disenchanted with respect to current urinal "ease of use" as well as spillage and costs. Notably, U.S. Pat. Nos. 1,458,640; 3,403,715 and 4,581,763.

The invention also relates to a container for receiving and retaining human discharged waste i.e. condoms as well as external catheters. Research suggest that there are no products on the market that adequately provide a solution to fill this need. Furthermore, the size of condoms and external catheters remains confusing and there are many misconceptions pertaining to proper "size". Hence, condom and external catheter selection are based on circumference of the penis and not length. The dilemma results in condom breakage and un-wanted corresponding pregnancies. Other entanglements include sexually transmitted diseases.

All in all, a need therefore exists for a male urinal apparatus which is ergonomic and designed with human factors in mind. Similarly, a need also exists for a condom-catheter disposable container . . . i.e. one that is bio-degradable and minimizes "flushing"; consequently, conserving water and avoiding water reclamation problems. In light of the aforementioned, an accompanied kit may very well be warranted for measurement fin order to facilitate proper sizing which ultimately ensures optimum operations of the invention.

SUMMARY OF THE INVENTION

The apparatus is a portable urinal container. Specifically, a device for bladder relief as well as for receiving feculent matter. In a first embodiment, the device is a cylinder having an outside layer made of impermeable plastic with a 1 way valve intended for apparatus re-use. In a second embodiment, an inside layer is made of cellulose sponge or synthetic absorbent material making it disposable after a single use. The device is generally shaped with a collar and pair of rounded corners along the back wall.

It is a further object of the invention to provide a custom-fit privacy drape coupled with a hook and loop fastener.

Still another object of the invention is to provide a penis measuring device (width) for selecting a proper fit and size urinal, condom, and/or external catheter.

These and other objects of the present invention, along with its' various features which characterize the apparatus . . . will become apparent upon further review of claims and specifications. For an even better understanding of the device, its operating advantages and specific features, a reference should be made to accompanying drawings illustrated herein. Collectively, the invention provides novelty and a significant improvement upon existing prior art related to male urinals as well as condom and external catheter measuring devices.

DETAILED DESCRIPTION

DESCRIPTION OF THE DRAWINGS

The invention will be more fully understood from the following detailed description taken in conjunction with the accompanying drawings in which.

DETAILED DESCRIPTION OF THE INVENTION

Figure 1:
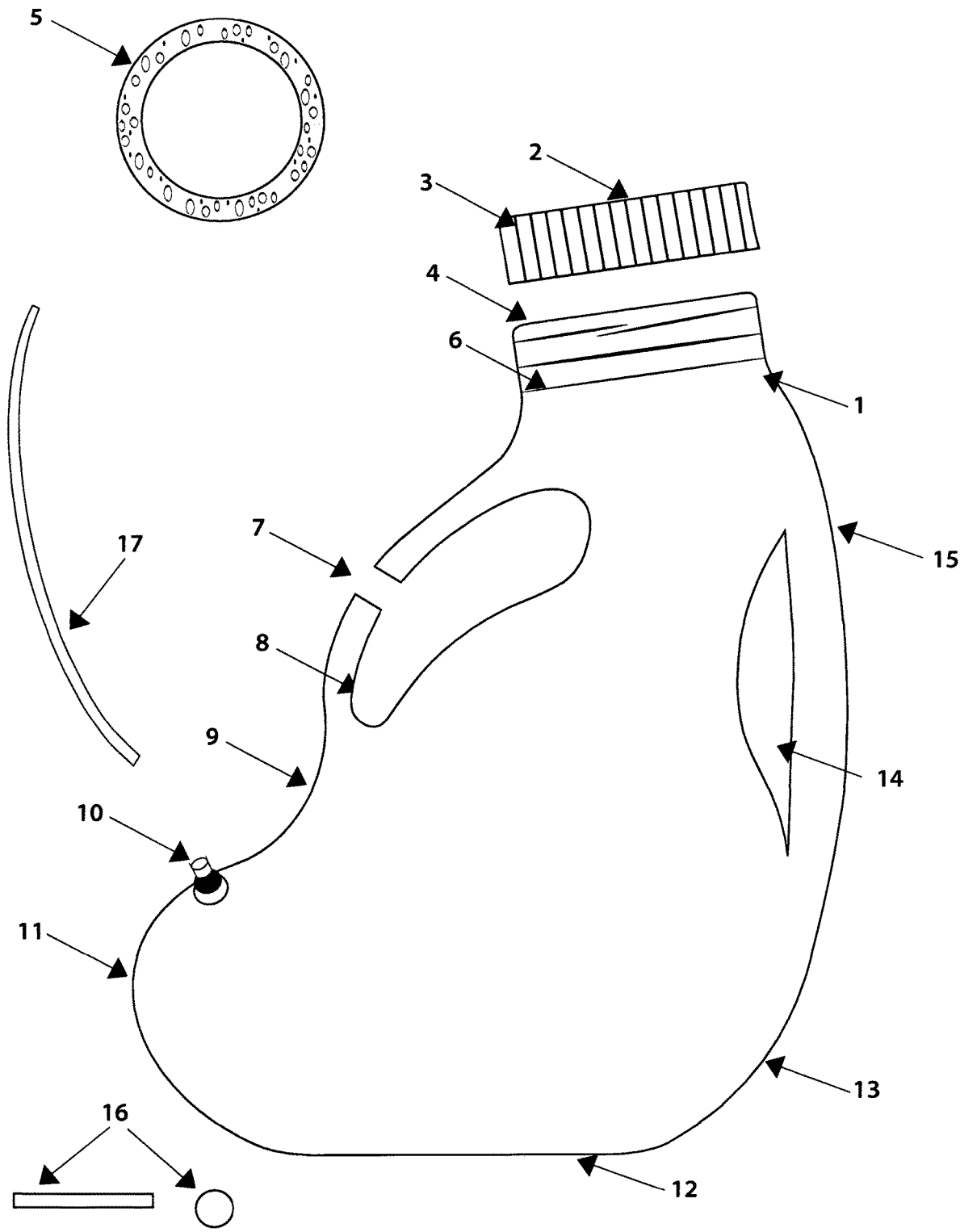
FIG. 1 is a side view of a portable piddle pod according to the invention
Figure 2:
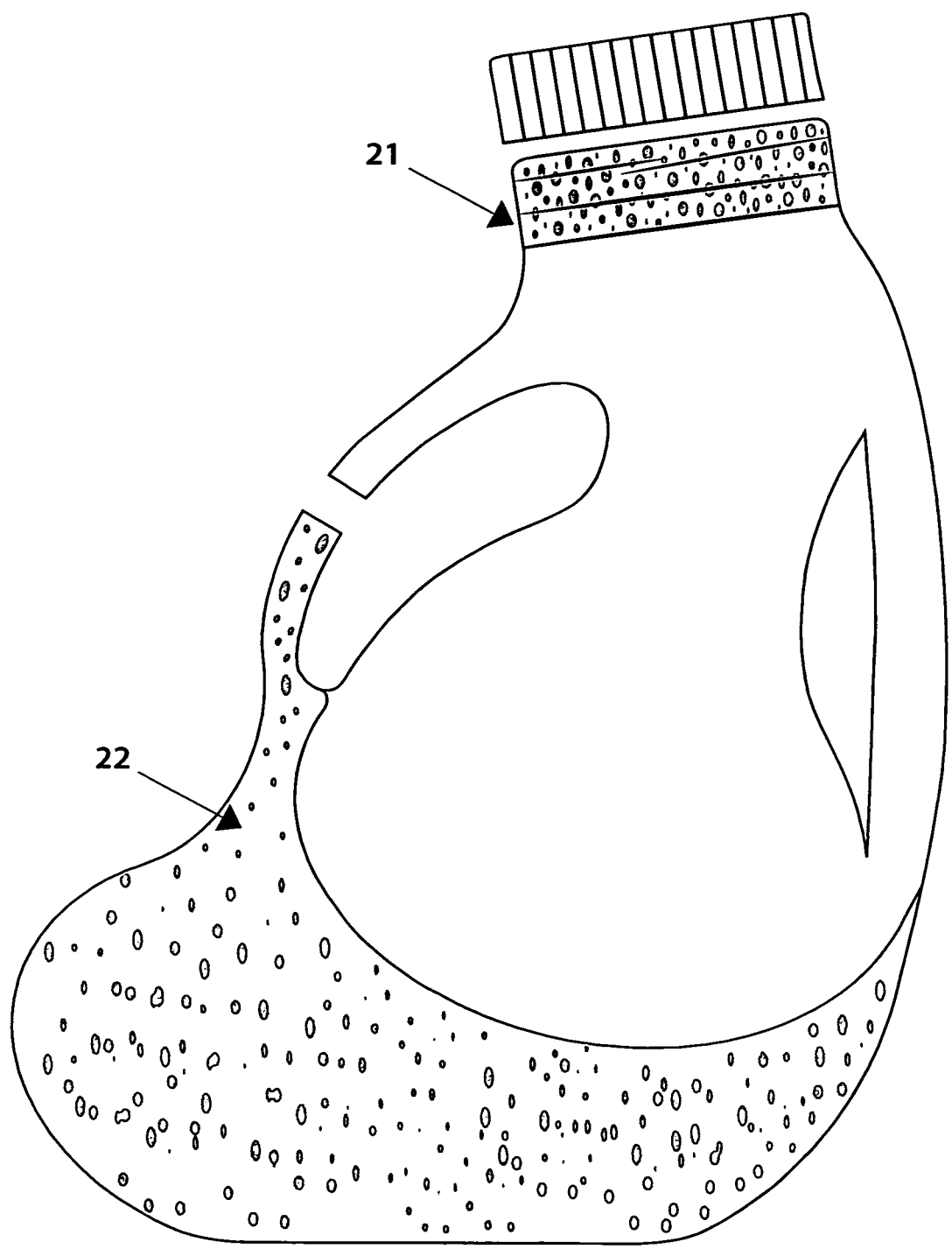
FIG. 2 is a side view of a portable urinal containing absorbent cellulose sponge material
Figure 3:
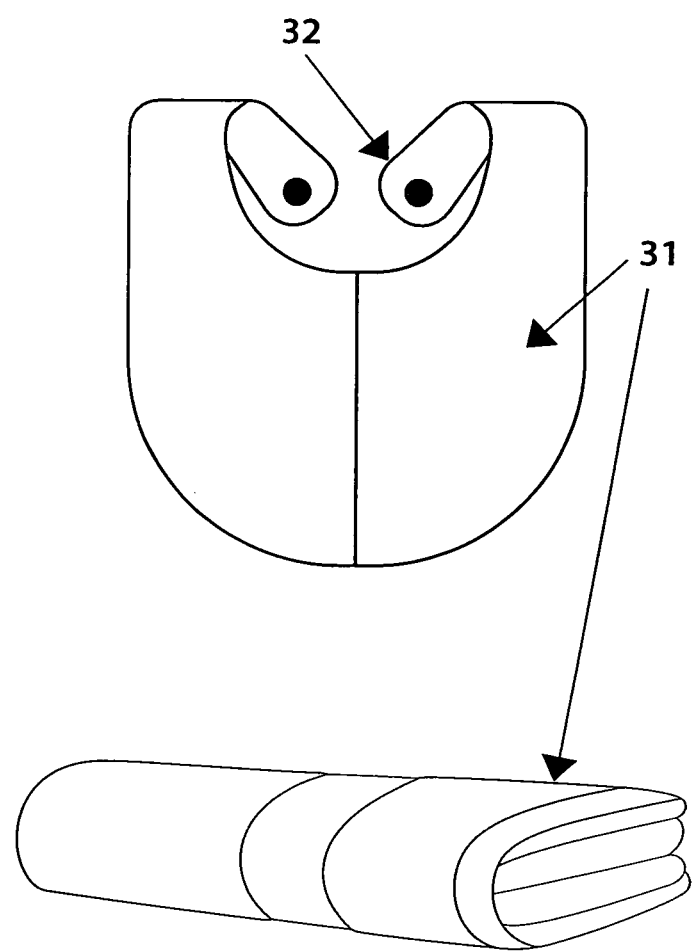
FIG. 3 is a front view of the privacy drape
Figure 4:
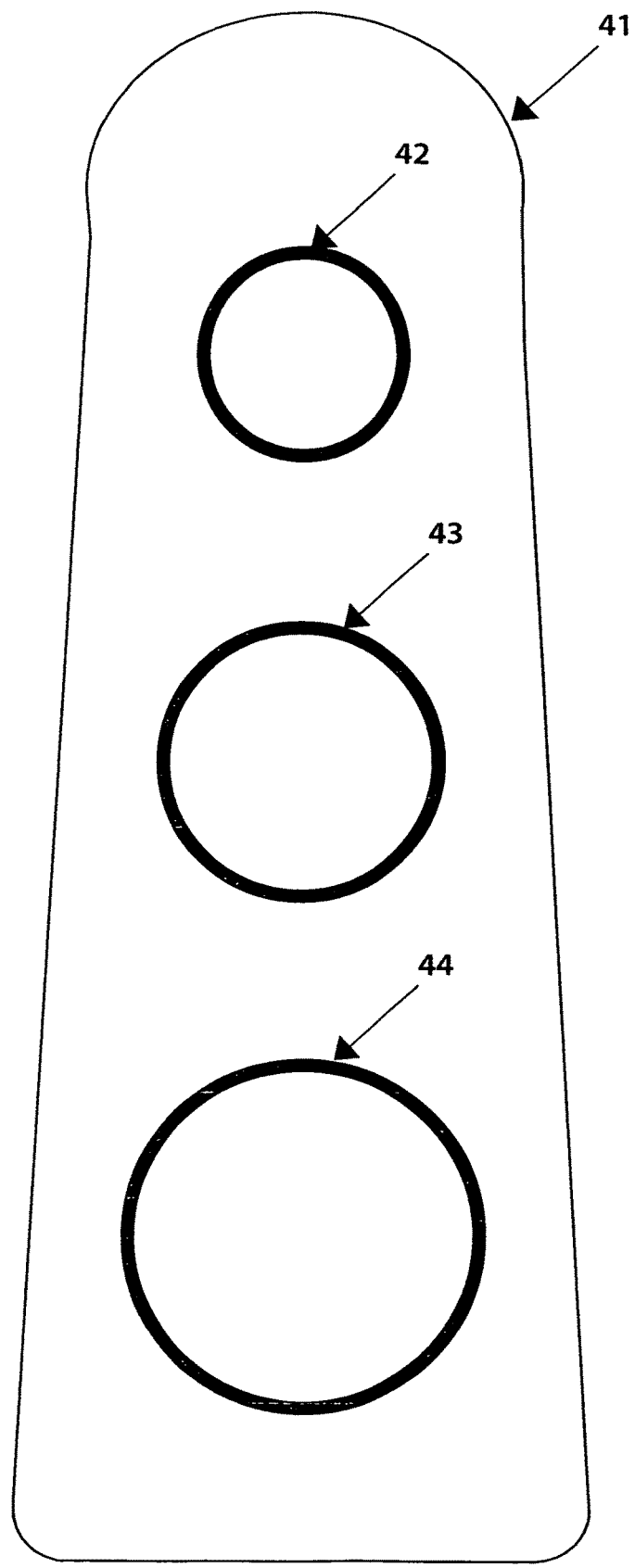
FIG. 4 is a front view of the urinal collar-penis measuring apparatus
Figure 5:
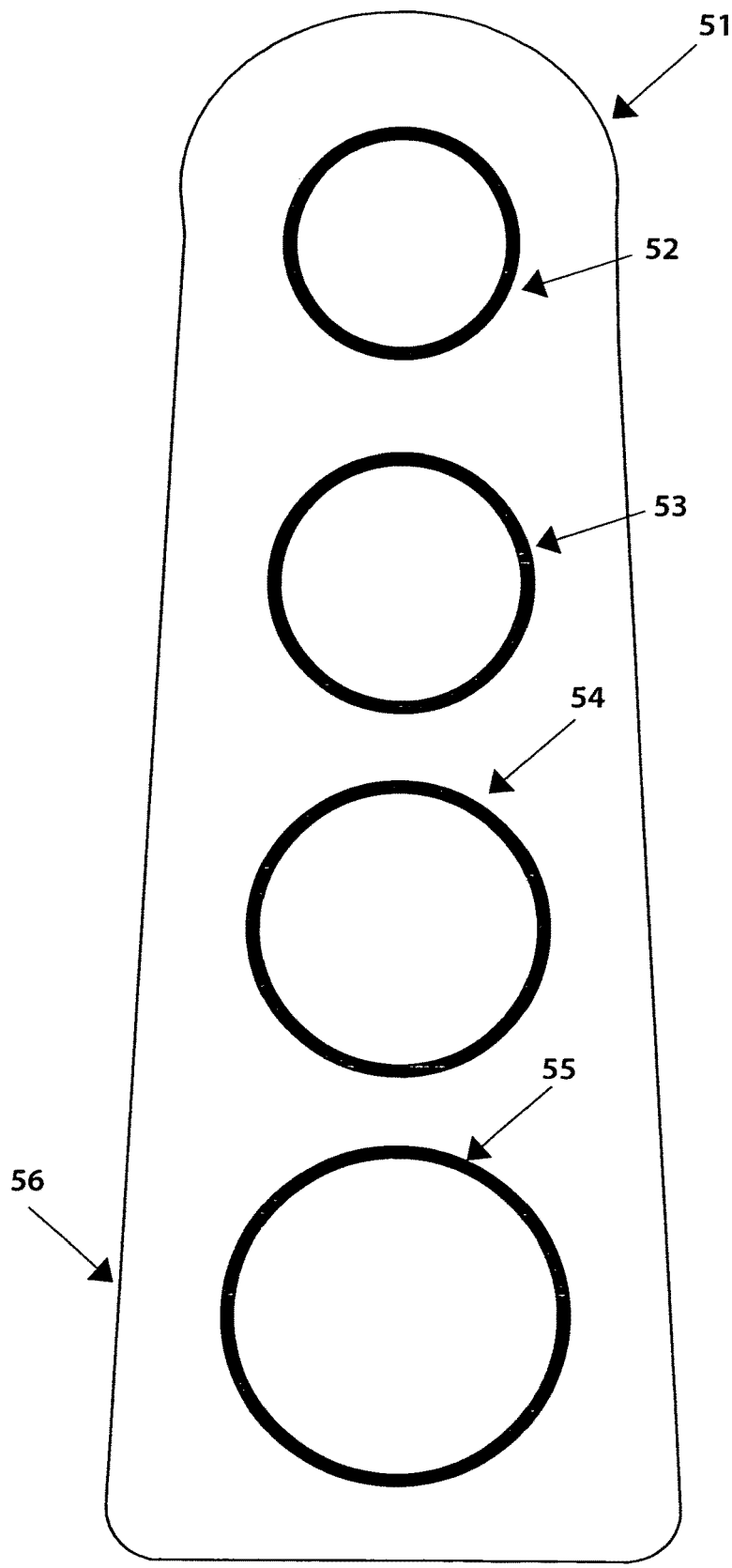
FIG. 5 is a front view of the condom-penis measuring apparatus
Figure 6:
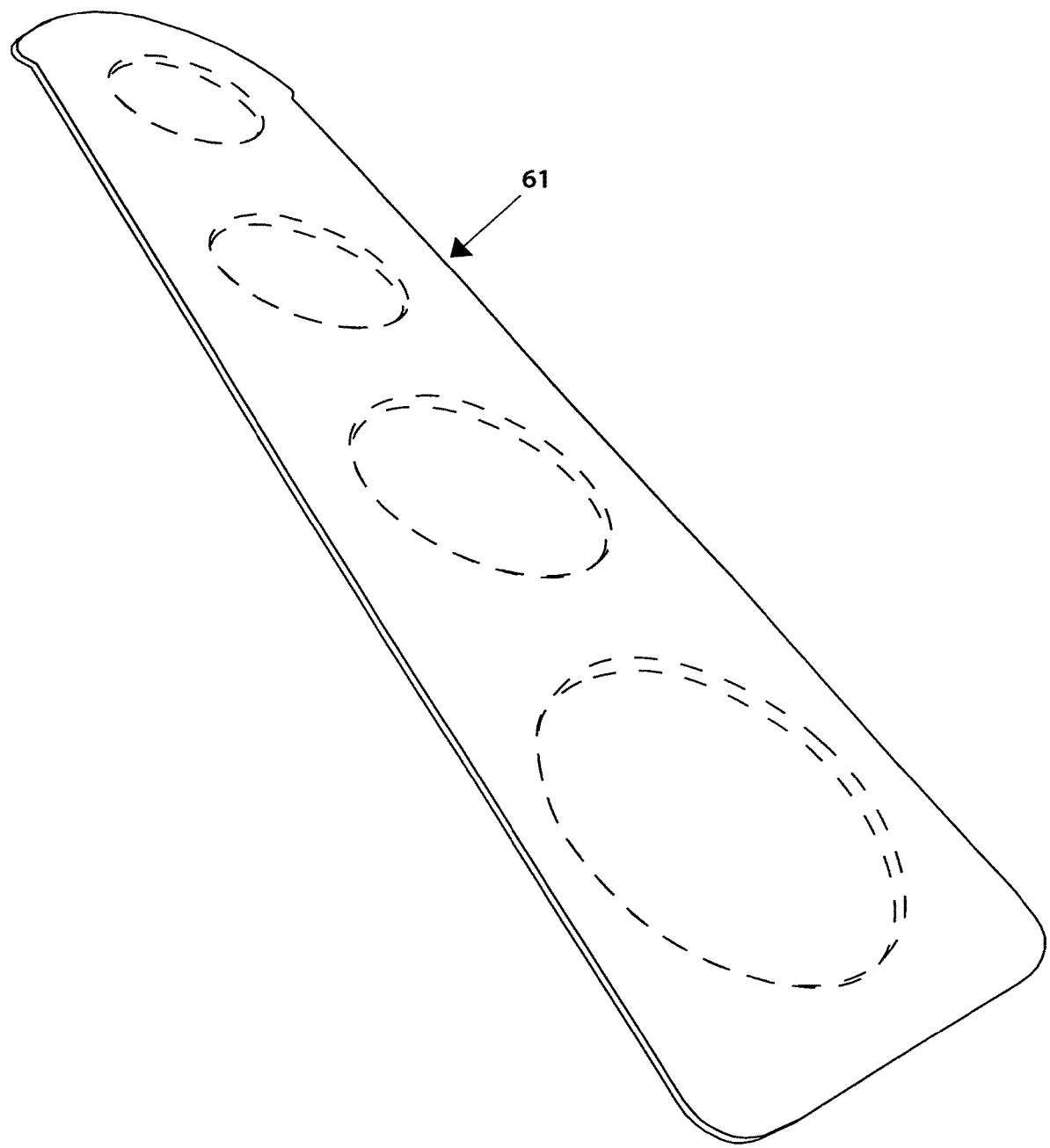
FIG. 6 is a cross-sectional side view of the condom-penis measuring apparatus of FIG. 5
Figure 7:
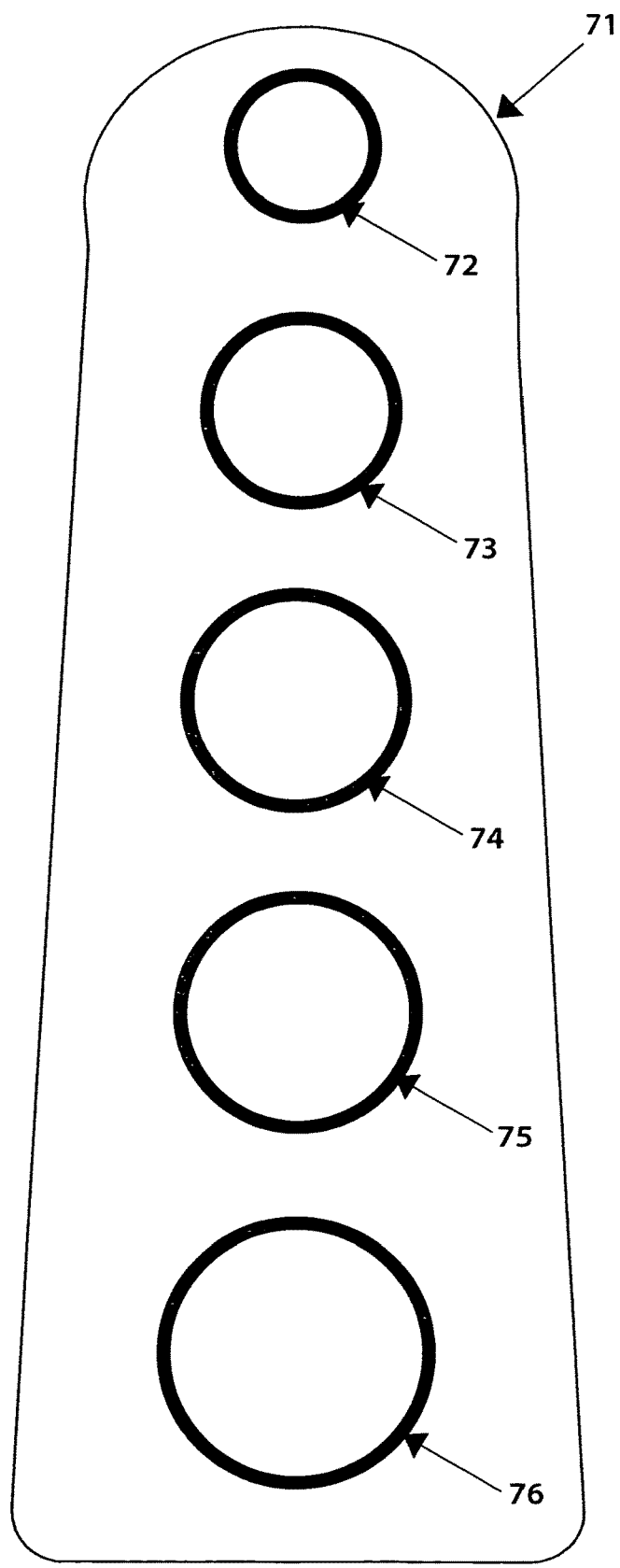
FIG. 7 is a front view of the external catheter-penis measuring apparatus

A portable piddle pod 1 according to the present invention is 9.5" long/7.5" wide and 4" across . . . illustrated in FIGS. 1-2. The urinal has an opening 4 at one end and a lid 2 with gripping ridges on said lid 3. The container collar has compressed sponge material 21 with a cross section view 5 that is approximately ¼" thick. The external collar opening is approximately 2.25" and has three threaded corrugations 6 in order to securely fasten lid that is approximately 2.75" in diameter and ⅞" in height. The apparatus is elongated with an opening in one of the handles 7 for securing to bed or golfing cart rail. At least a portion of the handle 8 is used to stabilize the piddle pod while in use. The lower curvature 9 is designed to conform to a standard size seat edge. After use, the one way valve 10 with a hose attachment 17 is used to empty the liquid from container as well as to clean without getting the "collar" sponge material wet.

The pod reservoir 11 is where the fluid source is stored. At least a portion of the bottom wall 12 is sufficiently flat so that the apparatus may be stood up in a horizontal position. When in use, the upper curvature 13 is designed to facilitate a flow to the back wall while minimizing splashing in doing so. A second handle 14 in conjunction with the first handle collectively adds to the containers stability. The front curvature 15 is an ergonomic design that optimizes penis position while maintaining a sitting posture coupled with a urine's upward flow incline tendency.

The device and placement on a vehicle's floor like an airplanes cockpit can be held in-part by utilizing a magnetic material along the exterior of back wall and/or neodymium magnets and hook and loop 16.

In cases where the container is intended to be disposed of after a single use . . . an absorbent sponge material is utilized along the back wall 22 area.

As part of the piddle pod kit, an ergonomic drape 31 has been designed in an effort to provide a mechanism that allows some privacy. In doing so, a hands-free effort is ideal in doing so, holding the towel in place is accomplished using a piece of hook and loop 32 as a temporary fastener.

Another tool in the piddle pod kit is the penis measurement device 41 with a measurement of 9.5"×3.5". The piddle pod comes in multiple sizes most notably small 42 with a diameter of 1.2", a medium size of 1.65" seen in 43, as well as a large size 44 that is 2.1". Said device is made of a plastic base with sterile rubber aperture rings.

If the apparatus 1 is used instead as a condom disposal container, the kit comes with a penis measurement device 51 as well in order to select the appropriate size prophylactic. Several erect sizes are possible; nevertheless, a measurement apparatus with general U.S. sizes contains 4 apertures: 52 small—is 1 5/16", 53 medium—is 1 1/2", 54 large—is 1 3/4", and 55 extra large—is 2". Said device is made of a plastic base with sterile rubber aperture rings. For teaching purposes, color can be used on the surface depicting the upper holes 52/53 in green, the large hole 54 in yellow, and the extra large size 55 in red. Furthermore, demarcation lines are used to measure the length despite the fact that condom sizes are measured by girth and not length. Moreover, a magnetic backing can be utilized for hanging on classroom wall 56. A perspective view of said apparatus is seen 61. Overall length 9.5"×width 3.5".

When the portable urinal 1 is used as a disposal container for exterior catheters . . . part of the kit is a measurement stick 71. The top of the apparatus is shaped much like a penis in that the top is bulb like. The aperture 72 is approximately 0.875"-1 1/16" diameter. In this case, the stick is used a medical instrument i.e. a tool used for indwelling—intermittent catheterization wherein the penis head spongiosum surface is gently pressed down with a repeated circular forward motion until the penis head is snuggly held in place. Noteworthy, the stick is also used for an uncircumcised penis in an effort to keep the foreskin retracted. For external catheters, the aperture 73 is used for small and/or 29 mm in diameter, 32 mm is used for medium 74, 36 mm is used for large 75, and 41 mm is used for extra large 76. Said device is made of a plastic base with sterile rubber aperture rings. Overall length 9.5"×width 3.5".

It will be apparent that while the preferred embodiment of this invention have been shown and described, various human factor modifications and changes may be made without departing from the true spirit and scope of the invention.

What is claimed:

1. A portable urination apparatus comprising:
   a collection container with an inlet top opening, a first and second curved sidewall, a flat bottom wall, and a reservoir, the inlet top opening having a collar with compressed sponge material and an exterior surface that includes threads: wherein the collection container has a pliable interior structure contoured to direct fluid flow wherein there is no impediment extending perpendicular to the first and second curved sidewall:
   a lid with gripping ridges configured to engage the collar to seal the apparatus:
   a first handle extending from an exterior surface of one of the first and second curved sidewalls, a second handle extending from an exterior surface of the other said first and second curved sidewalls, an opening in one of the handles configured for securing the apparatus to a bed or railing:
   a fluid passage extending from the collar to the reservoir, wherein the fluid passage has a narrowing section near the first and second handle and expanding at the reservoir: and
   wherein the bottom wall is configured to stand the apparatus upright when the bottom wall is in a horizontal position.

2. The apparatus of claim 1, further comprising a one way valve assembly.

3. The apparatus of claim 1, further comprises magnet strips or hook and loop fasteners configured to be attached to the bottom wall.

4. The apparatus of claim 1, further comprises an absorbent sponge material in the reservoir along the bottom wall.

\* \* \* \* \*